United States Patent
Rivers

(10) Patent No.: US 8,702,735 B2
(45) Date of Patent: Apr. 22, 2014

(54) ECCENTRIC ABRADING ELEMENT FOR HIGH-SPEED ROTATIONAL ATHERECTOMY DEVICES

(75) Inventor: Jody Rivers, Elk River, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 738 days.

(21) Appl. No.: 12/130,083

(22) Filed: May 30, 2008

(65) Prior Publication Data

US 2009/0299392 A1  Dec. 3, 2009

(51) Int. Cl.
*A61B 17/22* (2006.01)
*A61D 1/02* (2006.01)

(52) U.S. Cl.
USPC ............................................. 606/159

(58) Field of Classification Search
USPC ......... 606/159, 167, 170, 171, 180, 194, 200; 604/22
See application file for complete search history.

(56) References Cited

U.S. PATENT DOCUMENTS

| | | | |
|---|---|---|---|
| 4,445,509 A * | 5/1984 | Auth | 606/159 |
| 4,646,736 A | 3/1987 | Auth | |
| 4,728,319 A | 3/1988 | Masch | |
| 4,883,460 A | 11/1989 | Zanetti | |
| 4,935,025 A | 6/1990 | Bundy et al. | |
| 4,990,134 A | 2/1991 | Auth | |
| 5,007,896 A | 4/1991 | Shiber | |
| 5,026,384 A | 6/1991 | Farr et al. | |
| 5,030,201 A | 7/1991 | Palestrant | |
| 5,041,082 A | 8/1991 | Shiber | |
| 5,053,044 A * | 10/1991 | Mueller et al. | 606/159 |
| 5,078,723 A | 1/1992 | Dance et al. | |
| 5,116,352 A | 5/1992 | Schnepp-Pesch et al. | |
| 5,158,564 A | 10/1992 | Schnepp-Pesch et al. | |
| 5,192,291 A | 3/1993 | Pannek, Jr. | |
| 5,217,474 A | 6/1993 | Zacca et al. | |
| 5,224,945 A | 7/1993 | Pannek, Jr. | |
| 5,226,909 A | 7/1993 | Evans et al. | |
| 5,267,955 A | 12/1993 | Hanson | |
| 5,308,354 A | 5/1994 | Zacca et al. | |
| 5,372,602 A | 12/1994 | Burke | |
| 5,376,100 A | 12/1994 | Lefebvre | |
| 5,395,311 A | 3/1995 | Andrews | |
| 5,431,673 A | 7/1995 | Summers et al. | |
| 5,443,443 A | 8/1995 | Shiber | |

(Continued)

FOREIGN PATENT DOCUMENTS

| | | | |
|---|---|---|---|
| GB | 2426456 A * | 11/2006 | A61B 17/22 |
| WO | 2006/126176 | 11/2006 | |
| WO | WO2008/006708 | 1/2008 | |

*Primary Examiner* — Ryan Severson
*Assistant Examiner* — Katherine M Shi
(74) *Attorney, Agent, or Firm* — Winthrop & Weinstine, P.A.

(57) ABSTRACT

The invention provides a rotational atherectomy device having, in various embodiments, a flexible, elongated, rotatable drive shaft with at least one asymmetric and at least partially spherical abrading element attached thereto, which comprises an abrasive surface. The abrading element comprises more mass above the drive shaft than below and comprises a flattened side or transverse surface which creates hard cutting edges and spaces the center of mass radially from the rotational axis of the drive shaft. Thus the center of mass is moved vertically and transversely by the structure of the abrading element, conferring geometric and mass eccentricity upon the element. When placed against stenotic tissue and rotated at high speed, the eccentric nature of the abrading element moves along an orbital path, opening the lesion to a diameter larger than the resting diameter of the abrading element.

25 Claims, 7 Drawing Sheets

(56) References Cited

U.S. PATENT DOCUMENTS

| | | |
|---|---|---|
| 5,490,859 A | 2/1996 | Mische et al. |
| 5,501,694 A | 3/1996 | Ressemann et al. |
| 5,540,707 A | 7/1996 | Ressemann et al. |
| 5,556,408 A | 9/1996 | Farhat |
| 5,584,843 A | 12/1996 | Wulfman et al. |
| 5,632,755 A | 5/1997 | Nordgren et al. |
| 5,643,298 A | 7/1997 | Nordgren et al. |
| 5,667,490 A | 9/1997 | Keith et al. |
| 5,681,336 A | 10/1997 | Clement et al. |
| 5,836,868 A | 11/1998 | Ressemann et al. |
| 5,843,103 A | 12/1998 | Wulfman |
| 5,916,227 A | 6/1999 | Keith et al. |
| 5,938,670 A | 8/1999 | Keith et al. |
| 6,015,420 A | 1/2000 | Wulfman et al. |
| 6,080,171 A | 6/2000 | Keith et al. |
| RE36,764 E | 7/2000 | Zacca et al. |
| 6,146,395 A | 11/2000 | Kanz et al. |
| 6,152,938 A | 11/2000 | Curry |
| 6,206,898 B1 | 3/2001 | Honeycutt et al. |
| 6,258,052 B1 * | 7/2001 | Milo .............................. 604/22 |
| 6,270,509 B1 | 8/2001 | Barry et al. |
| 6,494,890 B1 | 12/2002 | Shturman et al. |
| 6,579,299 B2 | 6/2003 | McGuckin, Jr. et al. |
| 6,596,005 B1 | 7/2003 | Kanz et al. |
| 2003/0199889 A1 | 10/2003 | Kanz et al. |
| 2005/0149084 A1 | 7/2005 | Kanz et al. |

* cited by examiner

ECCENTRIC ABRADING ELEMENT FOR HIGH-SPEED ROTATIONAL ATHERECTOMY DEVICES

BACKGROUND OF THE INVENTION

1. Field of the Invention

The invention relates to devices and methods for removing tissue from body passageways, such as removal of atherosclerotic plaque from arteries, utilizing a high-speed rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patentcy of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) discloses another known atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. Though this atherectomy device possesses certain advantages over the Auth device due to its flexibility, it also is capable only of opening an artery to a diameter about equal to the diameter of the enlarged abrading surface of the drive shaft since the device is not eccentric in nature.

U.S. Pat. No. 6,494,890 (Shturman) discloses another known atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. In addition, some stenotic tissue may block the passageway so completely that the Shturman device cannot be placed therethrough. Since Shturman requires that the enlarged eccentric section of the drive shaft be placed within the stenotic tissue to achieve abrasion, it will be less effective in cases where the enlarged eccentric section is prevented from moving into the stenosis. Further, the enlarged eccentric section is biconical in profile which provides some advantages but also may confer some disadvantages in certain situations. The disclosure of U.S. Pat. No. 6,494,890 is hereby incorporated by reference in its entirety.

U.S. Pat No. 5,681,336 (Clement) provides a known biconical tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., 20,000-200,000 rpm. Essentially, the center of mass offset from the rotational axis of the drive shaft would result in development of significant centrifugal force, exerting too much pressure on the wall of the artery and creating too much heat and excessively large particles.

Each of the cutting and/or abrading elements described above comprise a center of mass that is, through modification of various parameters, positionable in such a way that it remains substantially collinear with a vertical line bisecting the element and intersecting at 90 degrees the rotational axis of the drive shaft to which the elements are attached or formed therefrom. Thus, these known devices provide the ability to manipulate the position of the center of mass of the element, but only along this bisecting vertical line that is normal, i.e., 90 degrees, to the drive shaft's axis of rotation. Thus the center of mass may be moved in a single dimension. It would be advantageous to enable positioning the center of mass of the cutting and/or abrading element in more than one dimension to facilitate enhanced achievement and provision of orbital motion during high-speed rotation.

The present invention overcomes these deficiencies and provides, interalia, the above-referenced improvements.

BRIEF SUMMARY OF THE INVENTION

The invention provides a rotational atherectomy device having, in various embodiments, a flexible, elongated, rotatable drive shaft with at least one at least partially spherical asymmetric abrading element attached thereto, which comprises an abrasive surface. The abrading element comprises more mass above the drive shaft than below and comprises a flattened side or transverse surface which creates hard cutting edges and spaces the center of mass radially from the rotational axis of the drive shaft. Thus the center of mass is moved vertically and transversely by the structure of the abrading element, conferring geometric and mass eccentricity upon the element. When placed against stenotic tissue and rotated at high speed, the eccentric nature of the abrading element moves along an orbital path, opening the lesion to a diameter larger than the resting diameter of the abrading element.

An object of the invention is to provide a high-speed rotational atherectomy device having at least one asymmetric, at least partially solid and partially spherical abrading element having at least one abrasive surface for abrading stenotic material.

Another object of the invention is to provide a high-speed rotational atherectomy device having at least one asymmetric, at least partially solid and partially spherical abrading element having at least one abrasive surface for abrading stenotic material and a proximal or distal transverse cutting edge for cutting stenotic material.

Another object of the invention is to manipulate the location of the center of mass of the abrading element in more than one dimension, preferably two or three dimensions, away from the approximate geometric center and/or axis of rotation of the drive shaft to which the abrading element is attached.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

Figure 1:
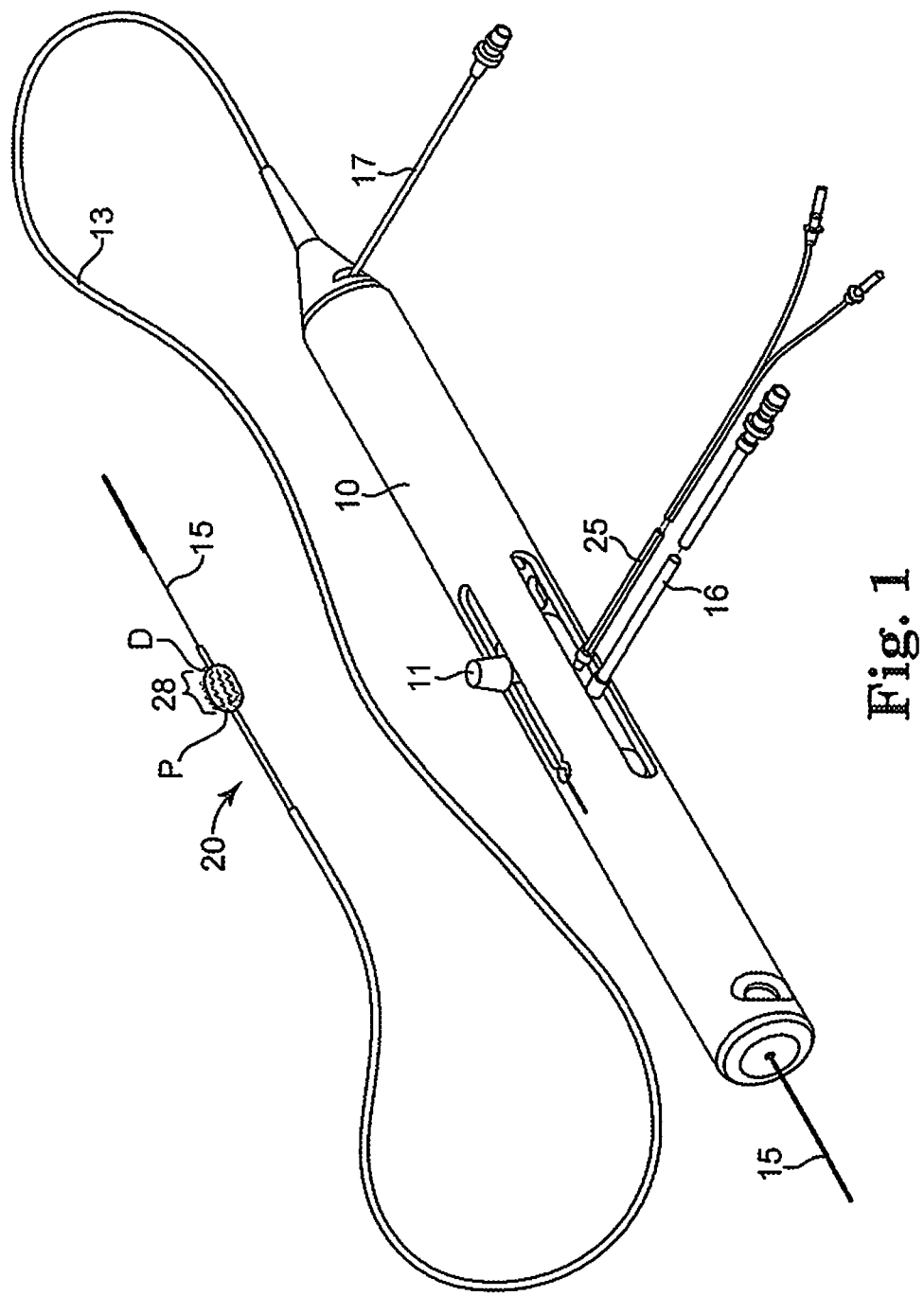
FIG. 1 is a perspective view of one embodiment of a rotational atherectomy device and system comprising one embodiment of the abrading element of the present invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

FIG. 1 illustrates one embodiment of a rotational atherectomy device and abrading element of the present invention. The device includes a handle portion 10, an elongated, flexible drive shaft 20 having an eccentric enlarged abrading head 28, and an elongated catheter 13 extending distally from the handle portion 10. The drive shaft 20 is constructed from helically coiled wire as is known in the art and the abrading head 28 is fixedly attached thereto. Further to the various embodiments of the drive shaft that are contemplated by the present invention, the drive shaft's helically coiled wire may comprise as few as three wires or as many as 15 wires and may have a right hand or a left hand winding as will be known to the skilled artisan. The catheter 13 has a lumen in which most of the length of the drive shaft 20 is disposed, except for the enlarged abrading head 28 and a short section distal to the abrading head 28. Abrading head 28 is asymmetric and eccentric, with its center of mass positionable in more than one dimension, more preferably in at least two dimensions, and most preferably in three dimensions relative to the approximate geometric center and/or rotational axis of the drive shaft as will be discussed further infra. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20 (details regarding such handles and associated instrumentation are well know in the industry, and are described, e.g., in U.S. Pat. No. 5,314,407, issued to Auth). The handle 10 also desirably includes a control knob 11 for advancing and retracting the turbine and drive shaft 20 with respect to the catheter 13 and the body of the handle.

Figure 2:
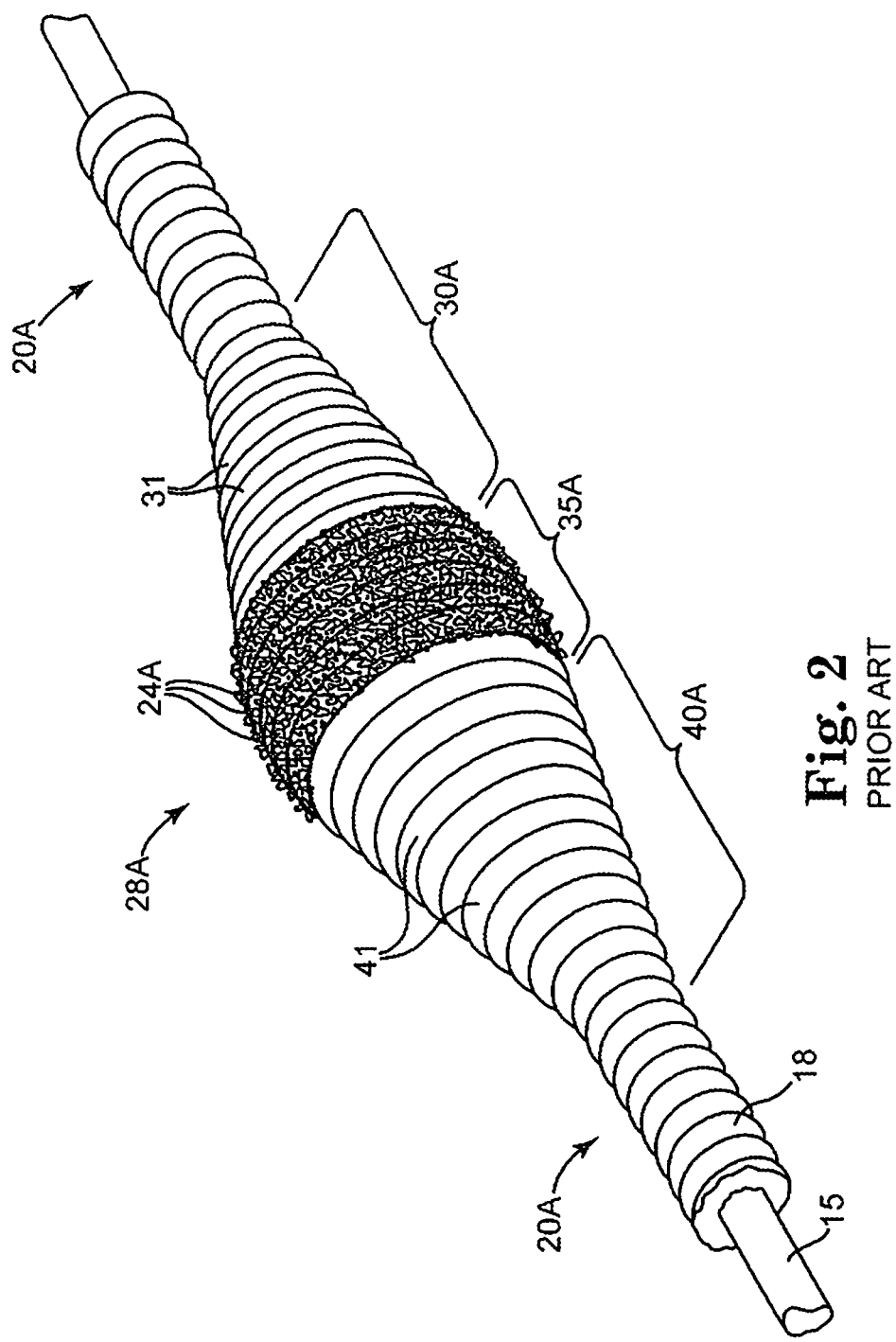
FIG. 2 is perspective, broken-away view of a prior art flexible eccentric abrading head formed from the drive shaft.
Figure 3:
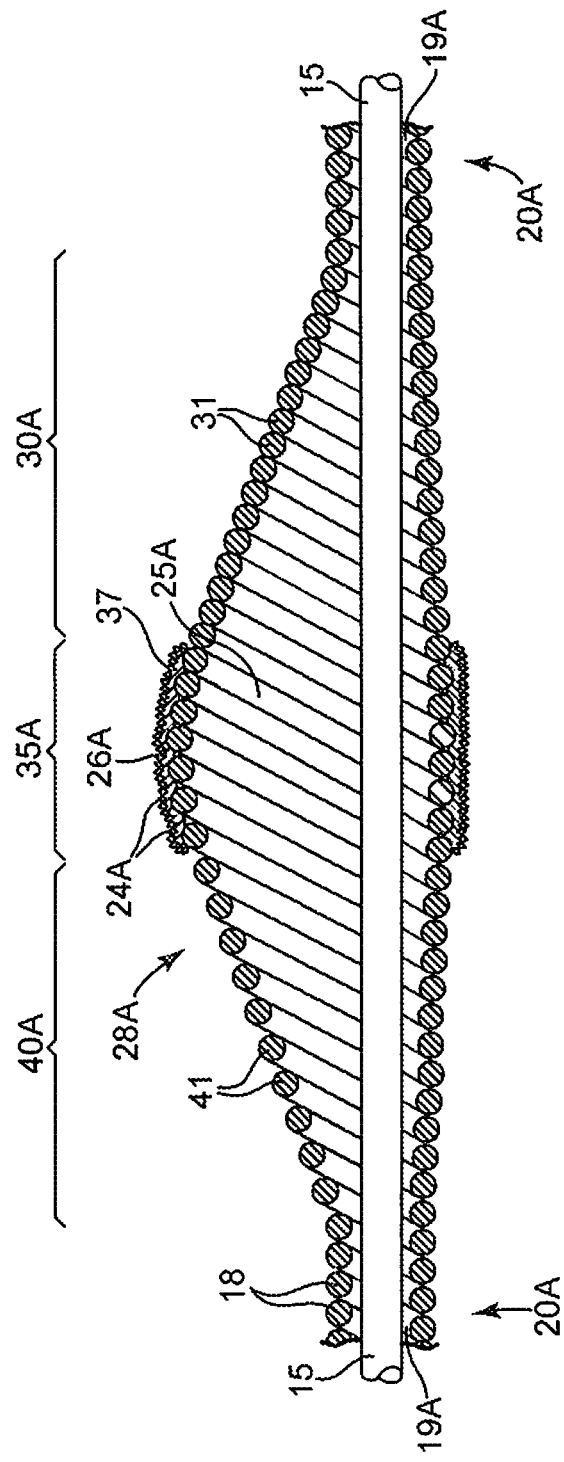
FIG. 3 is a broken-away, longitudinal cross-sectional view of a prior art eccentric abrading head formed from the drive shaft.
Figure 4:
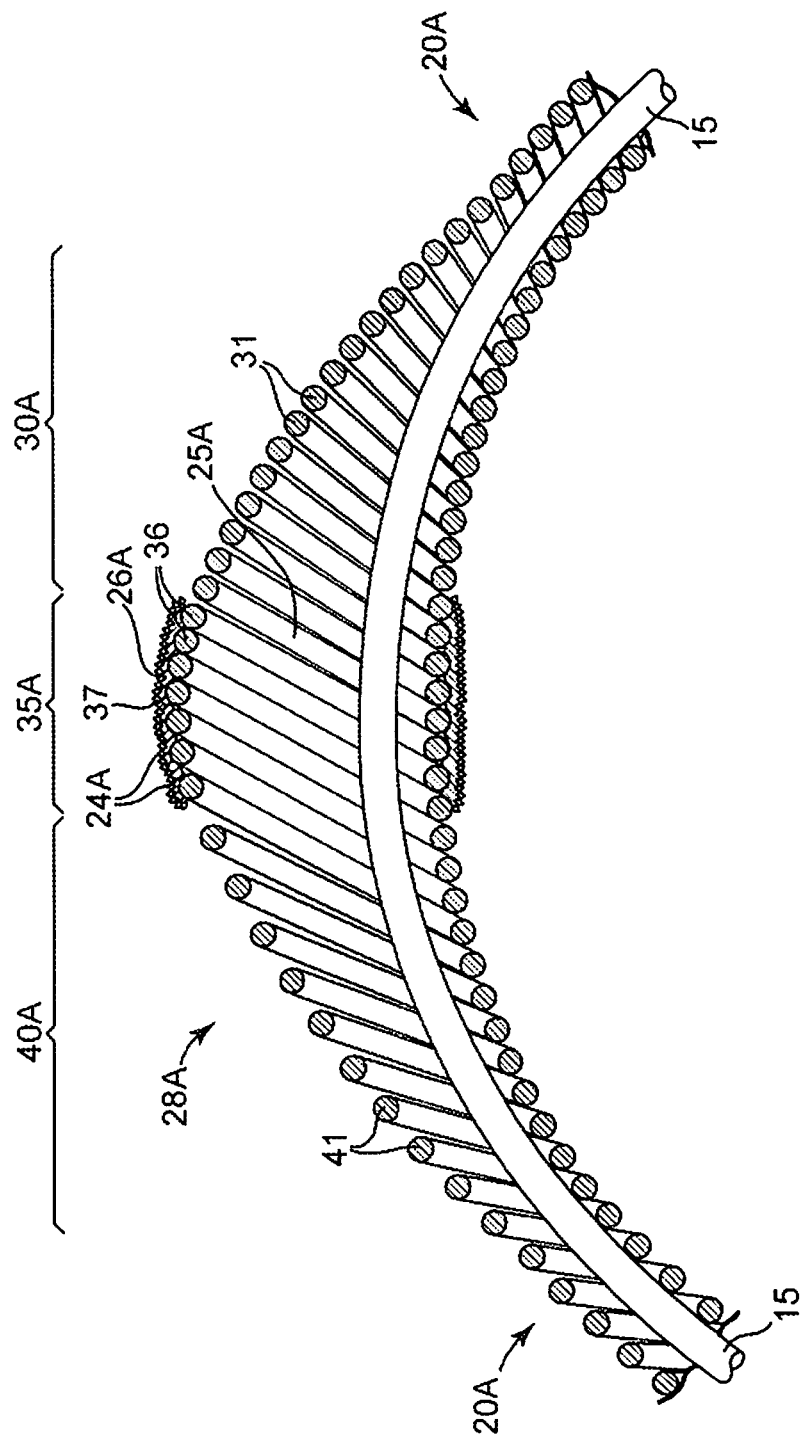
FIG. 4 is a broken-away, longitudinal cross-sectional view illustrating the flexibility of a prior art flexible eccentric enlarged abrading head formed from the drive shaft.

FIGS. 2-4 illustrate details of a known device comprising an eccentric enlarged diameter abrading section 28A of a drive shaft 20A. The drive shaft 20A comprises one or more helically wound wires 18 which define a guide wire lumen 19A and a hollow cavity 25A within the enlarged abrading section 28A. Except for the guide wire 15 traversing the hollow cavity 25A, the hollow cavity 25A is substantially empty. The eccentric enlarged diameter abrading section 28A includes, relative to the location of the stenosis, proximal 30A, intermediate 35A and distal 40A portions. Wire turns 31 of the proximal portion 30A of the eccentric enlarged diameter section 28A preferably have diameters that progressively increase distally at a generally constant rate, thereby forming generally the shape of a cone. Wire turns 41 of the distal portion 40A preferably have diameters that progressively decrease distally at a generally constant rate, thereby forming generally the shape of a cone. Wire turns 36 of the intermediate portion 35A are provided with gradually changing diameters to provide a generally convex outer surface which is shaped to provide a smooth transition between the proximal and distal conical portions of the enlarged eccentric diameter section 28A of the drive shaft 20A.

Continuing with the known device of FIGS. 2-4, at least part of the eccentric enlarged diameter abrading section of the drive shaft 28A (preferably the intermediate portion 35A) comprises an external surface capable of removing tissue. A tissue removing surface 37 comprising a coating of an abrasive material 24A to define a tissue removing segment of the drive shaft 20A is shown attached directly to the wire turns of the drive shaft 20A by a suitable binder 26A.

FIG. 4 illustrates the flexibility of the known eccentric enlarged diameter abrading section of the drive shaft 28A, shown with drive shaft 20A advanced over guide wire 15. In the embodiment shown, adjacent wire turns of the intermediate portion 35A of the eccentric enlarged cutting head of the drive shaft are secured to one another by the binding material 26A securing the abrasive particles 24A to the wire turns 36. Proximal portion 30A and distal 40A portion of the eccentric enlarged diameter section of the drive shaft comprise wire turns 31 and 41, respectively, are not secured to one another, thereby permitting such portions of the drive shaft to flex, as shown in the drawing. Such flexibility facilitates advancement of the device through relatively tortuous passageways and, in some embodiments, flexing of the eccentric enlarged diameter abrading section 28A during high-speed rotation. Alternatively, adjacent wire turns 36 of the intermediate portion 35A of the eccentric enlarged diameter abrading section 28A of the drive shaft may be secured to one another, thereby limiting the flexibility of abrading section 28A.

Figure 5:
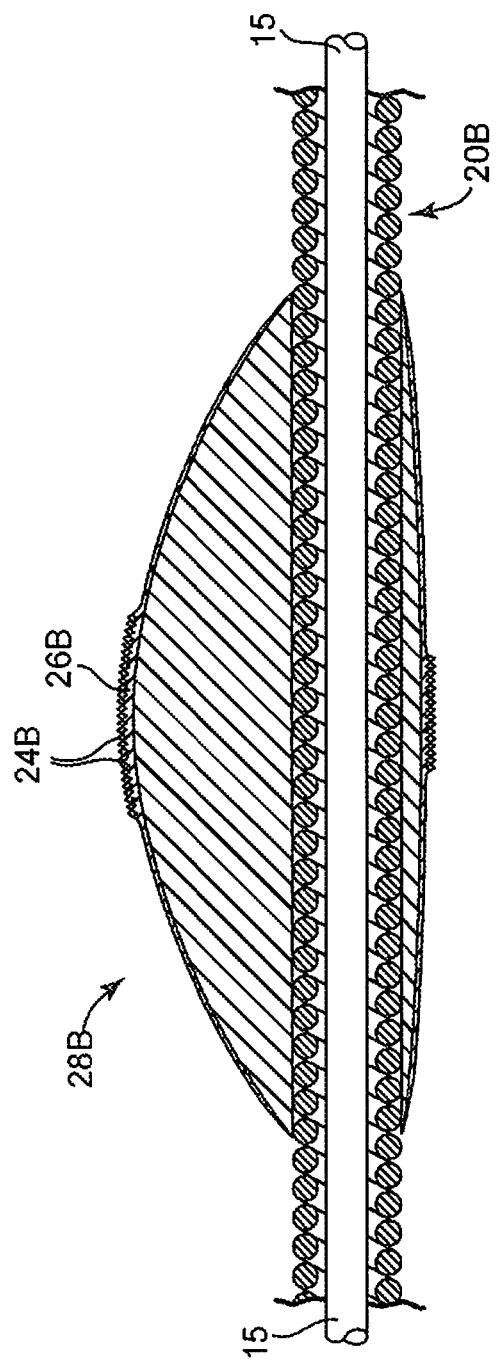
FIG. 5 is a longitudinal cross-sectional view of a prior art solid and inflexible eccentric and biconical abrasive burr attached to a drive shaft.

FIG. 5 illustrates another known rotational atherectomy device which employs a solid biconical abrasive burr 28B attached to a flexible drive shaft 20B, rotated over a guide wire 15 such as provided by U.S. Pat No. 5,681,336 to Clement. The drive shaft 20B may be flexible, however the solid biconical abrasive burr 28B is inflexible. The burr 28B has a coating of abrasive particles 24B secured to a portion of its outer surface by a suitable binding material 26B. This construction has limited utility, however because, as Clement explains at Col. 3, lines 53-55, the biconical and eccentric burr 28B must be rotated at "lower speeds than are used with high speed ablation devices, to compensate for heat or imbalance." That is, given both the size and mass of the solid burr-type construction, it is infeasible to rotate such a burr at the high speeds used during atherectomy procedures, i.e., 20,000-200,000 rpm. Essentially, the center of mass offset from the rotational axis of the drive shaft in this known device would result in development of significant centrifugal force, exerting too much pressure on the wall of the artery and creating too much heat, unnecessary trauma and excessively large particles. Further, the center of mass is manipulated in only a single dimension in this device.

Figure 6:
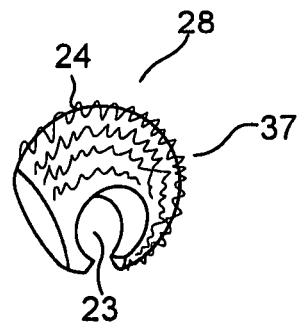
FIG. 6 is a rear perspective view of one embodiment of the present invention.
Figure 7:
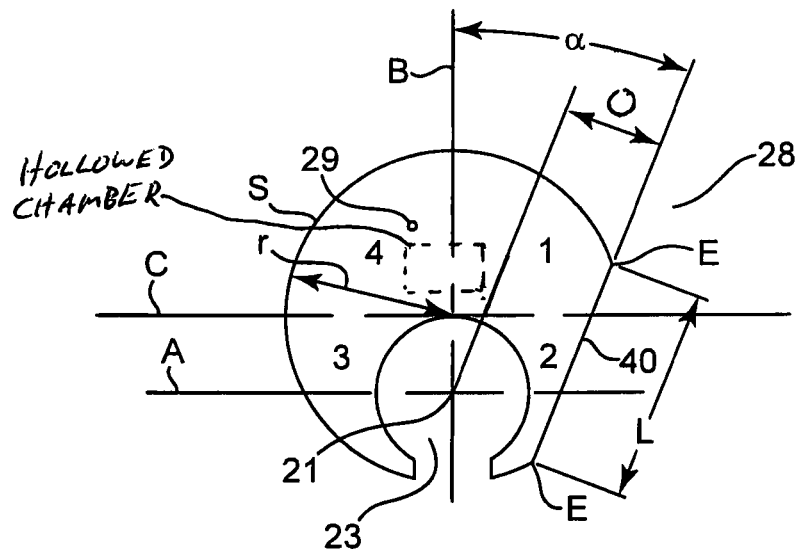
FIG. 7 is a front view of one embodiment of the present invention.

Turning now to FIGS. 6 and 7, one embodiment of the abrading element 28 of the rotational atherectomy device of the present invention will be discussed. The abrading head 28 may comprise at least one tissue removing surface 37 on the spherical external or outer surface S and/or on the flattened side surface 40 to facilitate abrasion of the stenosis during high speed rotation. The tissue removing surface 37 may comprise a coating of an abrasive material 24 bound to the external surface of at least a part of the spherical external surface and/or the external surface of the flattened side. The abrasive material may be any suitable material, such as diamond powder, fused silica, titanium nitride, tungsten carbide, aluminum oxide, boron carbide, or other ceramic materials. Preferably the abrasive material is comprised of diamond chips (or diamond dust particles) attached directly to the tissue removing surface(s) by a suitable binder—such attachment may be achieved using well known techniques, such as conventional electroplating or fusion technologies (see, e.g., U.S. Pat. No. 4,018,576). Alternately the external tissue removing surface may comprise mechanically or chemically roughening at least part of the external or outer surface(s) of the spherical surface S and/or the flattened side surface 40 to provide a suitable abrasive tissue removing surface 37. In yet another variation, the outer spherical surface S and/or flattened surface 40 may be etched or cut (e.g., with a laser) to provide small but effective abrading surfaces. Other similar techniques may also be utilized to provide a suitable tissue removing surface 37.

Continuing with reference to FIGS. 6 and 7, an at least partially enclosed lumen 23 may be provided through the enlarged abrading element 28 along the rotational axis 21 of the drive shaft for securing the abrading element 28 to the drive shaft 20 in a manner well known to those skilled in the art. See also FIG. 1 for an illustration of one embodiment of the abrading element 28 of the present invention attached to the drive shaft 20. In various embodiments, a hollowed chamber may be provided within the body of the abrading element 28 to lessen and manipulate the magnitude of mass (and position of the center of mass location relative to the drive shaft rotational axis 21) of the abrading element 28 to facilitate atraumatic abrasion and improve predictability of control of the orbital pathway and/or increase the rotational abrading and/or cutting diameter (orbital amplitude) of the abrading element 28 during high speed, i.e., 20,000 to 200,000 rpm, operation. As those skilled in the art will recognize, the orbital amplitude will be predictably manipulated based, inter alia, upon the positioning of the center of mass in relation to the rotational axis of the drive shaft, further manipulation techniques are discussed infra. Thus, a larger hollowed chamber, either symmetric or asymmetric in profile, will manipulate move the center of mass vertically closer to the rotational axis 21 than will a smaller hollowed chamber (or no hollowed chamber) and, at a given rotational speed, will create a smaller orbital amplitude and/or diameter for the abrading head 28 during high-speed rotation. In addition, the shape of hollowed chamber may effectively manipulate the position of the center of mass so that it may be transversely spaced from the rotational axis 21 and/or approximate geometric center of the drive shaft 20, and/or spaced proximally and/or distally along the rotational axis 21 and/or spaced from the approximate geometric center, as will be discussed further herein.

Specifically with reference to FIGS. 1 and 7, the drive shaft 20 has a rotational axis 21 which is coaxial with the guide wire 15, the guide wire 15 being disposed within the lumen (not shown) of the drive shaft 20, with abrading element 28 attached thereto. Abrading element 28 is illustrated with a proximal edge P and a distal edge D. The spherical portion of the abrading element 28 has an outer surface S which is substantially defined by a circle comprising a constant radius 4. The circular nature of the sphere's external or outer surface S is interrupted by a flattened side surface 40, wherein a section of the sphere has effectively been sliced away, leaving the flattened surface 40. The intersection of the flattened surface 40 and the spherical outer surface S may provide at least one hard edge E, therealong that may be used to facilitate cutting of stenotic material. Alternatively, such edge(s) E may be smoothed and or radiused in whole or in part to reduce trauma during the high-speed atherectomy procedures when abrading without cutting is desired.

Referring primarily now to FIG. 7, which illustrates a front view, looking down the rotational axis 21 of the drive shaft 20, of the inventive abrading element 28, we will now discuss the structures that allow the abrading element 28 of the present invention to achieve orbital motion during high-speed rotation. Lines A and B represent horizontal and vertical lines, respectively, in this embodiment that intersect at a 90 degree angle at the rotational axis 21 of the drive shaft. Line C is a horizontal line that intersects with Line B at a 90 degree angle. This intersection of Lines C and B in the illustrated embodiment represents the approximate geometric center of the abrading element 28 and forms the basis for defining four quadrants 1, 2, 3 and 4 within the abrading element 28 as illustrated. The approximate geometric center is located, for purposes of illustration at the intersection of Lines C and B, directly above the drive shaft axis of rotation 21. This approximate geometric center, as illustrated, would comprise the actual geometric center of a completely spherical object, i.e., abrading head. However, since the flattened side is a component of the present invention, it is recognized readily by the skilled artisan that the actual geometric center will be offset from the marked position of the approximate geometric center as illustrated and described, i.e., at the intersection of Lines C and B. Moreover, for an asymmetric abrasive section 28 of the present invention which comprises a shape that is not a regular geometric shape, the concept of "geometric center" can be approximated by locating the mid-point of the longest chord which is drawn through the rotational axis of the drive shaft and connects two points on a perimeter of a transverse cross-section taken at a position where the perimeter of the eccentric enlarged diameter section has its maximum length. Locating the approximate geometric center in this manner allows description of the relative location of the center of mass as will be easily understood by the skilled artisan.

The bulk of mass of the abrading element 28 is illustrated as being located above line C and above the rotational axis 21, thus positioning the center of mass 29 above line C and, as illustrated, above the rotational axis 21. Without further manipulation, the center of mass of the abrading element 28 would remain on Line B and/or above rotational axis 21.

The flattened surface 40 effectively removes and eliminates mass from what may be viewed as previously spherical quadrants 1 and 2 in the illustrated embodiment, whereby a slice of material has been removed from quadrants 1 and 2 to form the flattened surface 40. Those skilled in the art will recognize that the flattened surface 40 may be formed and positioned in either of quadrants 1, 2, 3 and/or 4. The embodiment illustrated effectively moves and spaces the center of mass 29 transversely away from center Line B and from the axis of rotation 21 of the drive shaft. Thus, in the embodiment of the inventive element 28 as illustrated, the center of mass 29 is spaced radially away from the axis of rotation 21 and transversely from the axis of rotation 21. In the illustrated case, the center of mass for the abrading element 28 will be in quadrant 4. Those skilled in the art will recognize that the flattened side may be disposed on either side of the element 28, thereby manipulating the center of mass 29 into either quadrant 1 or 4. Moreover, the amount of radial spacing achieved is dependent upon the differential of mass located above both Line C and the rotational axis 21.

Additional manipulation and positioning of the center of mass 29 may be achieved by modifying the angle of the flattened surface 40 with respect to the drive shaft's axis of rotation 21. In the embodiment illustrated, the flattened surface 40 is parallel to the drive shaft axis of rotation 21. Alternate embodiments may comprise a non-parallel relationship between the flattened surface 40 and the drive shaft axis of rotation 21. In this way, the center of mass 29 may be moved positioned accordingly within, as illustrated, quadrant 4.

As described above, the center of mass 29 position within the abrading element 28 of the present invention may be further manipulated by modifying the amount of mass (and its relative distribution) within the element 28 and, in particular, through modification of such mass and its distribution above the rotational axis 21 of the drive shaft 20. Thus, creation of a hollow space within the body of abrading element 28 will reduce the amount of mass and, if the hollow space is symmetric with respect to Lines A and B, will simply move the center of mass vertically downward along Line B, i.e., closer to the axis of rotation 21 of the drive shaft 20 as compared with a completely solid element 28. Further manipulation of the location and position of the center of mass 29 may be achieved by creating a hollowed space that is asymmetric with respect to either Lines A and/or B. In this embodiment, the center of mass 29 may be positioned along Line B, as above, but manipulated so that it is not centered between the proximal P and distal D edges of the abrading element 28. Instead, such manipulation may allow the center of mass 29 to move proximally, i.e., closer to proximal edge P, or distally, i.e., closer to distal edge D, along the axis of rotation 21 of the drive shaft. In addition, such manipulation may allow positioning of the center of mass 29 in either quadrants 1 or 4, or in extreme cases, even within quadrants 2 or 3. Such positional manipulation of the center of mass 29 may be achieved with the differential use of materials having different densities to manufacture the element 28 as well, either alone or in combination with additional techniques described herein, including but not limited to creation of a hollowed space within the element 28.

Moreover, the flattened side 40 comprises an angle α which represents the angle flattened side achieves with respect to vertical center Line B, with angle origin at the axis of rotation 21 and is disposed along the abrading head 28 a distance O from the rotational axis 21 of the drive shaft and a length L. Angle α may be increased or decreased, as shown the preferred angle α is approximately 21 degrees, though any angle between zero and 90 degrees may be utilized. Obviously a smaller angler α will tend to move the center of mass 29 closer to quadrant 3, i.e., lower within quadrant 4, and ultimately could drive the center of mass 29 into quadrant 3 if the angle α is sufficiently small. Further, distance O may be made larger or smaller as desired to manipulate the center of mass 29 positioning as will be well understood by the skilled artisan. Finally, length L will change as distance O changes; there is an inverse relationship between O and L. As O increases, L decreases and as O decreases, L increases. As the skilled artisan will understand given the disclosure thus far, the location of the center of mass 29 of abrading element 28 may be manipulated through modification of one or more of the following parameters: the amount and distribution of mass above the axis of rotation 21 relative to the amount of mass below the axis of rotation 21; the length L and distance O, and the angle α.

In addition, flattened side 40 may be positioned at virtually any point around the circumference of the outer spherical surface S of element 28, i.e., within one or more of quadrants 1, 2, 3, and/or 4. Obviously this provides another degree of freedom in the design and manipulation of the center of mass 29 positioning relative to the axis of rotation 21.

As will be described in greater detail below, offsetting the center of mass 29 from the drive shaft's axis of rotation 21 provides the abrading element 28 with an eccentricity that permits it to achieve orbital motion during high-speed rotation. Such orbital motion allows opening an artery to a diameter substantially larger than the nominal diameter, i.e., twice the radius r, of the abrading element 28, preferably the opened diameter is at least twice as large as the nominal resting diameter of the enlarged eccentric abrading element 28. In the case of the present invention, the center of mass 29 is offset from the axis of rotation 21 in more than one dimension, or more preferably in at least two dimensions, and most preferably in three dimensions. The more than one dimensional movement of the center of mass 29 may be vertically along Line B and transversely along Line C. Moreover, the center of mass 29 may be moved in a third dimension by manipulating the angle between the flattened surface and the rotational axis 21 of the drive shaft as well as through differential use of materials having different densities in the construction and manufacture of element 28 and by creating an asymmetric hollowed space within element 28 and/or positioning the flattened side 40 in selected locations along spherical outer surface S as described above. This third dimension of movement is, as the skilled artisan will now recognize, generally located along the axis of rotation 21 of the drive shaft.

It should be understood that, as used herein, the words "eccentric" and "asymmetric" are defined and used herein to refer to either a difference in location between the geometric center of the abrading element 28 and the rotational axis 21 of the drive shaft 20, or to a difference in location between the center of mass 29 of the abrading element 28 and the rotational axis 21 of the drive shaft 20. Either such difference, at the proper rotational speeds, will enable the abrading element 28 to open a stenosis to a diameter substantially greater than the nominal diameter of the asymmetric and eccentric abrading element 28.

The abrading element 28 of the rotational atherectomy device of the invention may be constructed of stainless steel, tungsten or similar material.

The extent to which a stenosis in an artery can be opened to a diameter larger than the nominal diameter of the eccentric abrading element 28 of the present invention depends on several parameters, including the radius of the eccentric abrading element 28, the mass of the eccentric abrading element 28, the distribution of that mass and, therefore, the location of the center of mass 29 within the eccentric abrading element 28 with respect to the rotational axis 21 of the drive shaft, and the speed of rotation.

The speed of rotation is a significant factor in determining the centrifugal force with which the tissue removing surface of the asymmetric abrading element 28, is pressed against the stenotic tissue, thereby permitting the operator to control the rate of tissue removal. Control of the rotational speed also allows, to some extent, control over the maximum diameter to which the device will open a stenosis. Applicants have also found that the ability to reliably control the force with which the tissue removing surface is pressed against the stenotic tissue not only permits the operator to better control the rate of tissue removal but also provides better control of the size of the particles being removed.

Figure 8:
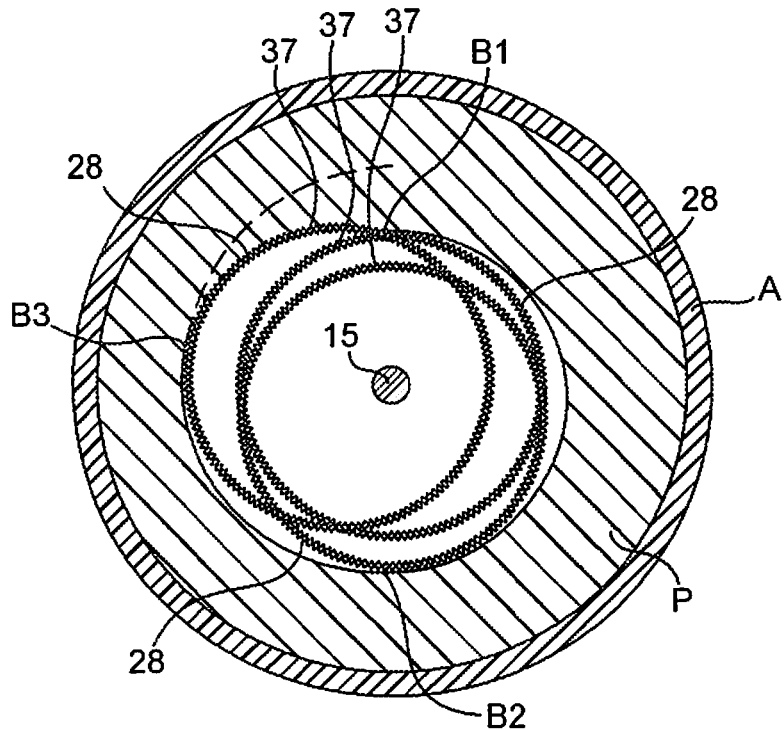
FIG. 8 is a transverse cross-sectional view illustrating three different positions of the rapidly rotating eccentric abrasive element of an eccentric rotational atherectomy device of the invention.
Figure 9:
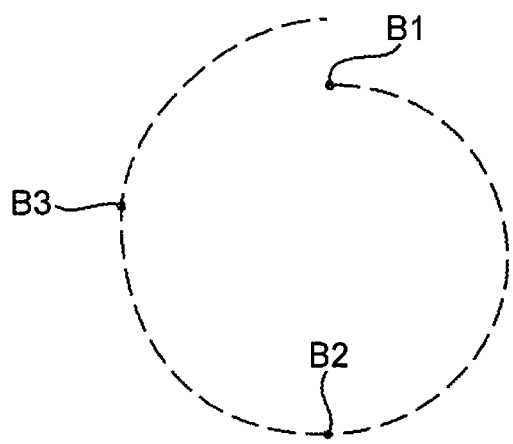
FIG. 9 is a schematic diagram illustrating the three different positions of the rapidly rotating eccentric abrasive element of an eccentric rotational atherectomy device of the invention shown in FIG. 8.

FIG. 8 illustrates the generally spiral orbital path taken by various embodiments of the eccentric abrading element 28 of the present invention, the abrading element 28 shown relative to the guide wire 15 over which the abrading element 28 has been advanced. The pitch of the spiral path is exaggerated for illustrative purposes—in reality, each spiral path of the abrading element 28 removes only a very thin layer of tissue via the tissue removing surface 37, and many, many such spiral passes are made by the eccentric abrading element 28 as the device is repeatedly moved forward and backward across the stenosis to fully open the stenosis. FIGS. 8 and 9 show schematically three different rotational positions of the abrading element 28 of a rotational atherectomy device of the invention. At each position the abrasive surface of the eccentric abrading element 28 contacts the plaque "P" to be removed—the three positions are identified by three different points of contact with the plaque "P", those points being designated in the drawing as points B1, B2, and B3. Notice that at each point it is generally the same portion of the abrasive surface of the abrading element 28 that contacts the tissue—the portion of the tissue removing surface 37 that is radially most distant from the rotational axis of the drive shaft.

Although not wishing to be constrained to any particular theory of operation, applicants believe that offsetting the center of mass from the axis of rotation and positioning the center of mass eccentrically with respect to the approximate geometric center produces an "orbital" movement of the eccentric abrading element 28, the diameter of the "orbit" being controllable by varying, inter alia, the rotational speed of the drive shaft. Whether or not the "orbital" movement is as geometrically regular as is shown in FIGS. 8 and 9 has not been determined, but applicants have empirically demonstrated that by varying the rotational speed of the drive shaft one can control the centrifugal force urging the tissue removing surface 37 of the eccentric abrading element 28 against the surface of the stenosis. The centrifugal force can be determined according to the formula:

$$F_c = m\Delta x(\pi n/30)^2$$

where $F_c$ is the centrifugal force, m is the mass of the eccentric enlarged abrading element, $\Delta x$ is the distance between the center of mass of the eccentric abrading element 28 and the rotational axis of the drive shaft, and n is the rotational speed in revolutions per minute (rpm). Controlling this force $F_c$ provides control over the rapidity with which tissue is removed, control over the maximum diameter to which the device will open a stenosis, and improved control over the particle size of the tissue being removed.

Operationally, using the rotational atherectomy device of the invention the abrading element 28 may be repeatedly moved distally and proximally through the stenosis. By changing the rotational speed of the device he or she is able to control the force with which the tissue removal surface is pressed against the stenotic tissue, thereby being able to better control the speed of the plaque removal as well as the particle size of tissue removed. Since the stenosis is being opened to a diameter larger than the nominal diameter of the eccentric abrading element 28, the cooling solution and the blood are able to constantly flow around the enlarged abrading element. Such constant flow of blood and cooling solution constantly flushes away removed tissue particles, thus providing uniform release of removed particles, once the abrading element has passed through the lesion once.

The eccentric enlarged abrading element 28 may comprise a maximum cross-sectional diameter ranging between about 0.05 mm to about 3.0 mm. Thus, the eccentric enlarged abrading element may comprise cross-sectional diameters including, but not limited to: 0.05 mm, 0.075 mm, 0.1 mm, 0.5 mm, 1.0 mm, 1.25 mm, 1.50 mm, 1.75 mm, 2.0 mm, 2.25 mm, 2.50 mm, 2.75 mm, and 3.0 mm. Those skilled in the art will readily recognize that the incremental increases of mm within the above-listing of cross-sectional diameter are exemplary only, the present invention is not limited by the exemplary listing and, as a result, other incremental increases in cross-sectional diameter are possible and within the scope of the present invention.

Preferably the design parameters, e.g., inter alia, cross-sectional diameter, location of flattened surface 40 on the spherical outer surface 40, mass distribution within the element 28 and above Line C, magnitude of angle α, length of distance O and length L of flattened surface 40, and the angle between flattened surface 40 and the drive shaft axis of rotation 21 are selected so that the eccentric abrading element 28 is sufficiently eccentric that, when rotated over a stationary guide wire 15 (held sufficiently taut so as to preclude any substantial movement of the guide wire) at a rotational speed greater than about 20,000 rpm, at least a portion of its tissue removing surface 37 may rotate through a path (whether or not such path is perfectly regular or circular) having a diameter larger than the maximum nominal diameter of the eccentric abrading element 28. For example, and without limitation, for an enlarged abrading element 28 having a maximum cross-sectional diameter between about 0.05 mm and about 3.0 mm, at least a portion of the tissue removal surface 37 may rotate through a path having a diameter at least about 10% larger than the maximum nominal diameter of the eccentric abrading element 28, preferably at least about 15% larger than the maximum nominal cross-sectional diameter of the eccentric abrading element 28, and most preferably at least about 20% larger than the maximum nominal diameter of the eccentric abrading element 28.

Preferably design parameters are selected so that the eccentric abrading element 28 is sufficiently eccentric that, when rotated over a stationary guide wire 15 at a speed between about 20,000 rpm and about 200,000 rpm, at least a portion of its tissue removing surface 37 rotates through a path (whether or not such path is perfectly regular or circular) with a maximum diameter that is substantially larger than the maximum nominal diameter of the eccentric abrading element 28. In various embodiments, the present invention is capable of defining a substantially orbital path with a maximum diameter that is incrementally between at least about 50% and about 400% larger than the maximum nominal cross-sectional diameter of the eccentric abrading element 28. Desirably such orbital path comprises a maximum diameter that is between at least about 200% and about 400% larger than the maximum nominal diameter of the eccentric abrading element 28.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A high-speed rotational atherectomy device for opening a stenosis in an artery having a given diameter, comprising:
   a guide wire having a maximum diameter less than the diameter of the artery;
   a flexible elongated, rotatable drive shaft advanceable over the guide wire, the drive shaft having a rotational axis; and
   one asymmetric abrading element having a lumen therethrough and attached to the drive shaft thereby and having an approximate geometric center, the abrading element consisting of a spherical outer surface, one flattened surface interrupting the spherical outer surface at a distance from the drive shaft and its axis of rotation, and a hard edge therebetween, the abrading element further consisting of a center of mass that is eccentrically positioned in up to three dimensions relative to the approximate geometric center of the abrading element.

2. The rotational atherectomy device of claim 1, wherein the abrading element further comprises a tissue removal surface on at least a portion of the spherical outer surface and/or the flattened side surface.

3. The rotational atherectomy device of claim 1, wherein the edge between the spherical outer surface and the flattened side surface is smoothed.

4. The rotational atherectomy device of claim 1, further comprising the flattened side surface and the rotational axis of the drive shaft being parallel to one another.

5. The rotational atherectomy device of claim 1, further comprising the flattened side surface and the rotational axis of the drive shaft being non-parallel to one another.

6. The rotational atherectomy device of claim 1, further comprising an angle between the flattened side surface and a vertical line that intersects the rotational axis of the drive shaft, wherein the angle eccentrically positions the center of mass within the abrading element, the angle being between 0 and 90 degrees.

7. The rotational atherectomy device of claim 1, further comprising the flattened surface having a length that eccentrically positions the center of mass within the abrading element.

8. The rotational atherectomy device of claim 1, further comprising a distance from the axis of rotation of the drive shaft to the flattened surface that eccentrically positions the center of mass within the abrading element.

9. The rotational atherectomy device of claim 1, further comprising the flattened surface having a location that may be positioned with respect to the axis of rotation of the drive shaft to locate the flattened surface in at least one of quadrants 1, 2, 3 and/or 4 in order to eccentrically position the center of mass within the abrading element.

10. The rotational atherectomy device of claim 1, further comprising at least one hollow space within the abrading element in order to eccentrically position the center of mass within the abrading element.

11. The rotational atherectomy device of claim 10, wherein the at least one hollow space is asymmetric.

12. The rotational atherectomy device of claim 10, wherein the at least one hollow space is symmetric.

13. The rotational atherectomy device of claim 1, wherein the abrading element further comprises materials having different densities in order to eccentrically position the center of mass within the abrading element.

14. A high-speed rotational atherectomy device for opening a stenosis in an artery having a given diameter, comprising:
   a guide wire having a maximum diameter less than the diameter of the artery;
   a flexible elongated, rotatable drive shaft advanceable over the guide wire, the drive shaft having a rotational axis; and
   one asymmetric abrading element attached to the drive shaft, the abrading element consisting of:
   a spherical outer surface with a constant radius, one flattened surface interrupting the spherical outer surface at a distance from the drive shaft and its axis of rotation, and an edge therebetween, and an approximate geometric center, the abrading element further consisting of a tissue removing surface and a center of mass that is eccentrically positioned in three dimensions relative to the approximate geometric center of the abrading element, an angle between the flattened side surface and a vertical line through the rotational axis of the drive shaft that eccentrically positions the center of mass within the abrading element, wherein the flattened side surface and the rotational axis of the drive shaft are in a non-parallel relationship with one another, the flattened surface having a length that eccentrically positions the center of mass within the abrading element, a distance from the axis of rotation of the drive shaft to the flattened side surface that eccentrically positions the center of mass within the abrading element, the flattened side surface having a location that may be positioned with respect to the axis of rotation of the drive shaft in order to eccentrically position the center of mass within the abrading element.

15. The rotational atherectomy device of claim 14, further comprising at least one hollow space within the abrading element in order to eccentrically position the center of mass within the abrading element.

16. The rotational atherectomy device of claim 15, wherein the abrading element further comprises materials having different densities in order to eccentrically position the center of mass within the abrading element.

17. An abrading element affixed to a rotational drive shaft having an axis of rotation for use in atherectomy procedures, consisting of:
   a spherical outer surface having a constant radius;
   one flattened surface interrupting the spherical outer surface at a distance from the drive shaft and its axis of rotation;
   an approximate geometric center;
   a center of mass that is eccentrically positioned in up to three dimensions relative to the approximate geometric center of the abrading element by at least the interruption of the spherical outer surface by the flattened surface;
   an at least partially enclosed lumen defined through the abrading element, the drive shaft disposed therethrough and the abrading element affixed to the drive shaft thereby; and
   at least one hollow space within the abrading element in order to further eccentrically position the center of mass within the abrading element.

18. The rotational atherectomy device of claim 17, wherein the abrading element further comprises a tissue removal surface on at least a portion of the spherical outer surface and/or the flattened surface.

19. The abrading element of claim 17, further comprising the flattened surface and the rotational axis of the drive shaft being parallel to one another.

20. The rotational atherectomy device of claim 17, further the flattened surface and the rotational axis of the drive shaft being non-parallel to one another.

21. The rotational atherectomy device of claim 17, further comprising the flattened side surface having a length that eccentrically positions the center of mass within the abrading element.

22. The rotational atherectomy device of claim 17, further comprising the flattened surface having a location that may be positioned with respect to the axis of rotation of the drive shaft in order to eccentrically position the center of mass within the abrading element, wherein the center of mass may be positioned within one or more of quadrants 1, 2, 3 and 4 of abrading element.

23. The rotational atherectomy device of claim 17, wherein the at least one hollow space is asymmetric.

24. The rotational atherectomy device of claim 17, wherein the at least one hollow space is symmetric.

25. The rotational atherectomy device of claim 17, wherein the abrading element further comprises materials having different densities in order to eccentrically position the center of mass within the abrading element.

* * * * *